United States Patent
Patterson

[11] 3,975,378
[45] Aug. 17, 1976

[54] 20-CYANO-20,21-EPOXY STEROIDS

[75] Inventor: John W. Patterson, Mountain View, Calif.

[73] Assignee: Syntex (U.S.A.) Inc., Palo Alto, Calif.

[22] Filed: June 27, 1975

[21] Appl. No.: 590,776

[52] U.S. Cl. ................... 260/239.55 D; 424/241
[51] Int. Cl.$^2$ ............................................. C07J 17/00
[58] Field of Search .................... 260/239.55 D
/Machine Searched Steroids

[56] References Cited
UNITED STATES PATENTS 3,758,686  9/1973  Sieger et al. ............... 260/239.55 D
3,892,856  7/1975  Hill et al. ................... 260/239.55 D Primary Examiner—Elbert L. Roberts
Attorney, Agent, or Firm—Tom M. Moran

[57] ABSTRACT

Novel compounds useful as anti-inflammatories are represented by the formula

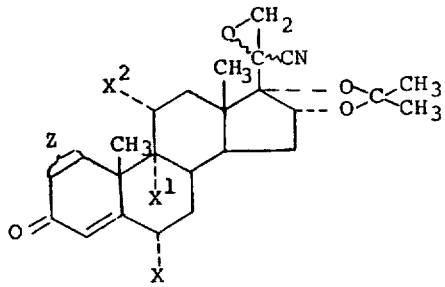

wherein Z is a single or double bond; X and $X^1$ are independently H, F or Cl; and $X^2$ is OH or when $X^1$ is Cl $X^2$ may also be Cl. The compounds are prepared by reacting a suitable 21-hydrocarbon sulfonate steroid with an alkali cyanide.

21 Claims, No Drawings

20-CYANO-20,21-EPOXY STEROIDS

BACKGROUND OF THE INVENTION

1. Field of the Invention

This invention relates to novel, anti-inflammatory 20-cyano-20,21-oxido steroids which are valuable in the treatment of inflammed conditions. These steriods are prepared by a novel process and are employed to prepare novel, effective pharmaceutical formulations.

Prior Art

U.S. Pat. No. 2,813,860 to Lincoln and Hogg, patented Nov. 19, 1957 discloses anti-gonal hormones which are useful as emulsifiers. The compounds of the U.S. Pat. No. 2,813,860 are progesterones and are entirely different from the novel compounds of this invention. By the process of that patent HCN is added to an α-halo-20-keto-progesterone to produce a 20 cyanohydrin which is then converted, in the presence of base, to a 20,21-or a 17,20-oxide-20-cyano steroid. The process of this invention is entirely different.

SUMMARY OF THE INVENTION

The primary aspect of this invention is the class of compounds represented by the formula

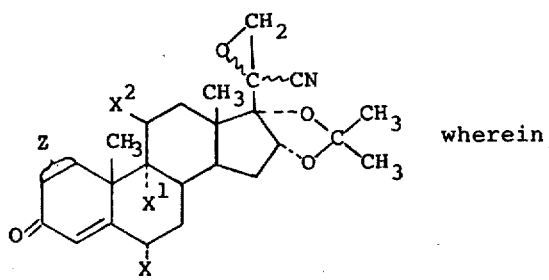

wherein

Z is double or single bond;
X is H, F or Cl;
$X^1$ is Cl, F, or H;
$X^2$ is OH or when $X^1$ is Cl, $X^2$ may be Cl.

Another aspect of this invention is the combination of the above defined novel compounds with suitable pharmaceutical excipients to form a topical, anti-inflammatory composition.

Still another aspect of this invention is a method for treating an inflammed skin condition in animals by contacting the inflammed area with an effective amount of a novel compound of this invention.

Still another aspect of this invention is a process of preparing the novel compounds of this invention which comprises reacting a 21-hydrocarbon sulfonate steroid with a suitable cyanide salt to form the steroid compounds defined above.

PREFERRED EMBODIMENTS

Compounds of the Invention

The compounds encompassed within the scope of this invention are those compounds chosen from the group represented by the formula

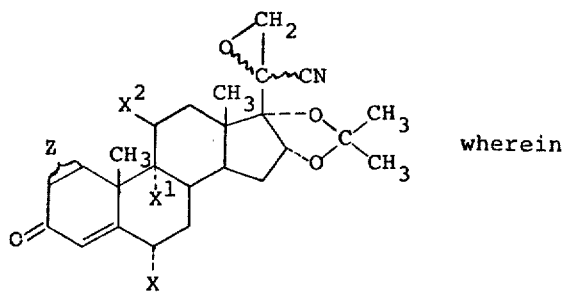

wherein

Z is double or single bond;
X is H, F or Cl;
$X^1$ is Cl, F, or H;
$X^2$ is OH or when $X^1$ is Cl, $X^2$ may be Cl. Thus, compounds falling within the scope of this invention are represented by the following names employing the rules set out by the INTERNATIONAL UNION OF PURE AND APPLIED CHEMISTRY (IUPAC) NOMENCLATURE OR ORGANIC CHEMISTRY SECOND EDITION, BUTTERWORTHS, 1966;

9α-chloro-20-cyano-20,21-epoxy-11β-hydroxy-16α,17α-propylidenedioxy-pregna-1,4-dien-3-one;
9α-chloro-20-cyano-20,21-epoxy-11β-hydroxy-16α,17α-propylidenedioxy-pregn-4-en-3-one;
20-cyano-20,21-epoxy-6α-fluoro-11β-hydroxy-16α,17α-propylidendioxy-pregna-1,4-dien-3-one;
20-cyano-20,21-epoxy-6α-fluoro-11β-hydroxy-16α,17α-propylidenedioxy-pregn-4-en-3-one;
6α-chloro-20-cyano-20,21-epoxy-11β-hydroxy-16α,17α-propylidenedioxy-pregna-1,4-dien-3-one;
6α-chloro-20-cyano-20,21-epoxy-11β-hydroxy-16α,17α-propylidenedioxy-pregn-4-en-3-one;
20-cyano-20,21-epoxy-9α-fluoro-11β-hydroxy-16α,17α-propylidenedioxy-pregna-1,4-dien-3-one;
20-cyano-20,21-epoxy-9α-fluoro-11β-hydroxy-16α,17α-propylidenedioxy-pregn-4-en-3-one;
20-cyano-20,21-epoxy-6α,9α-difluoro-11β-hydroxy-16α,17α-propylidenedioxy-pregna-1,4-dien-3-one;
20-cyano-20,21-epoxy-6α,9α-difluoro-11β-hydroxy-16α,17α-propylidenedioxy-pregn-4-en-3-one;
6α-chloro-20-cyano-20,21-epoxy-9α-fluoro-11β-hydroxy-16α,17α-propylidenedioxy-pregna-1,4-dien-3-one;
6α-chloro-20-cyano-20,21-epoxy-9α-fluoro-11β-hydroxy-16α,17α-propylidenedioxy-pregn-4-en-3-one;
20-cyano-20,21-epoxy-11β-hydroxy-16α,17α-propylidenedioxy-pregna-1,4-dien-3-one;
20-cyano-20,21-epoxy-11β-hydroxy-16α,17α-propylidenedioxy-pregn-4-en-3-one;

9α,11β-dichloro-20-cyano-20,21-epoxy-16α,17α-propylidene-dioxy-pregna-1,4-dien-3-one;
9α,11β-dichloro-20-cyano-20,21-epoxy-16α,17α-propylidene-dioxy-pregn-4-en-3-one;
9α,11β-dichloro-20-cyano-20,21-epoxy-6α-fluoro-16α,17α-propylidenedioxy-pregna-1,4-dien-3-one;
9α,11β-dichloro-20-cyano-20,21-epoxy-6α-fluoro-16α,17α-propylidenedioxy-pregn-4-en-3-one;
6α,9α,11β-trichloro-20-cyano-20,21-epoxy-16α,17α-propylidene-dioxy-pregna-1,4-dien-3-one;
6α,9α,11β-trichloro-20-cyano-20,21-epoxy-16α,17α-propylidene-dioxy-pregn-4-en-3-one;
9α-chloro-20-cyano-20,21-epoxy-6α-fluoro-11β-hydroxy-16α,17α-propylidenedioxy-pregna-1,4-dien-3-one;
9α-chloro-20-cyano-20,21-epoxy-6α-fluoro-11β-hydroxy-16α,17α-propylidenedioxy-pregn-4-en-3-one;
6α,9α-dichloro-20-cyano-20,21-epoxy-11β-hydroxy-16α,17α-propylidenedioxy-pregna-1,4-dien-3-one;
6α,9α-dichloro-20-cyano-20,21-epoxy-11β-hydroxy-16α,17α-propylidenedioxy-pregn-4-en-3-one;

Preferably, the compounds are defined by the group represented by the above formula wherein Z is a double or single bond; X is H or F; $X^1$ is H, F or Cl; and $X^2$ is OH or may be Cl when $X^1$ is Cl. Even more preferably is the group of compounds represented by the above formula wherein A is a double bond; X is F, $X^1$ is F or Cl; and $X^2$ is OH or may be Cl when $X^1$ is Cl.

As will be recognized by one acquainted with the sterochemistry of compounds similar to those of this invention, there is an asymmetric carbon at the 20 position of the molecule. In the preparation of the compounds of this invention, a mixture is obtained which is a mixture of both the 20R- and 20S- isomers in about a proportion of about 1:1. It is to be understood that both the 20R- and 20S- isomers alone as well as mixtures of two fall within the scope of this invention.

The 20-isomers are readily separable by chromatographic techniques and are distinguishable by their differences in melting points. Generally, the melting point of an isomer of a steroid of this invention may vary slightly with, i.a. the solvent system used for recrystallization. Thus, the melting points given for the 20-isomers are those obtained with the solvent systems indicated. Slight variations from the melting points given may be obtained using other solvent systems.

Method of Preparation

Generally the compounds of this invention are prepared by reacting the 21-hydroxy steroid with a suitable hydrocarbon sulfonyl chloride under conditions to form a 21-hydrocarbon sulfonate which is then reacted with a metal cyanide salt to form the 20 cyano-20,21-epoxy steroid compound of this invention. The process is set forth in the following reaction scheme wherein
Z is a double or single bond;
X and $X^1$ are independently H, F or Cl;
$X^2$ is OH or when $X^1$ is Cl, $X^2$ may also be Cl;
$RSO_2Cl$ is a hydrocarbon sulfonyl chloride; and
MCN is a suitable metal cyanide.

The hydrocarbon sulfonyl chloride useful for forming the intermediate II may be any suitable hydrocarbon sulfonyl chloride represented by methane sulfonyl chloride (mesyl chloride) or toluene sulfonyl chloride (tosyl chloride). Thus the intermediate II may be a 21-mesylate or 21-tosylate. The intermediates (II) are prepared from the corresponding 21 hydroxy compound (I) by reacting at low temperatures the 21-hydroxy steroid in a suitable solvent with, e.g. methane sulfonyl chloride. Low temperatures are generally from about +10° to −40°C and preferably will be about −15°C to about −25°C. Generally it is found that at low temperatures, that is, between −15° and −25°C the presence of a hydroxy at a position other than 21 (particularly 11β-hydroxy group) does not hinder the reaction and there is no competing reaction with the hydroxy at that position. The reaction takes place in a suitable solvent which is preferably an organic solvent which is slightly basic by the addition of a base such as an amine or which solvent is basic itself. Thus, the reaction can be run in pyridine as a solvent or it may be run in a mixture of another organic solvent with pyridine or another base. The base is present in reaction system to assist in the neutralization of the hydrochloric acid which is formed. Preferably the reaction is run in a mixture of a chlorinated hydrocarbon solvent such as chloroform or methylene chloride with a suitable organic base such as triethyl amine. After a suitable reaction time, the 21-mesylate is formed which is then reacted with the sodium cyanide as discussed hereafter. Generally the formation of the 21-mesylate will take place in a matter of less than 5 hours, preferably will take no more than about 30 minutes to prepare.

Compounds which may be reacted with, e.g. methanesulfonyl chloride to form the mesylate which in turn may be reacted to form the compounds of this invention are chosen from the group represented by formula I above.

Suitable metal cyanides for reacting with the intermediate sulfonate (II) include alkali metal cyanides for example, lithium, sodium, or potassium, cyanide or alkali earth metal cyanide such as beryllium, magnesium, or calcium cyanide and the like. Because of its availability and ease of reaction sodium cyanide is preferred. The reaction of the sulfonate with sodium cyanide is carried out in a suitable polar, aprotic, organic solvent such as dimethylformamide, dimethylsulfoxide, sulfolane, methylpyrrolidone, hexamethylphosphoramide and the like. Although other solvents such as alcohols may be used the reaction in such solvents is substantially slower, and thus is not preferred. The

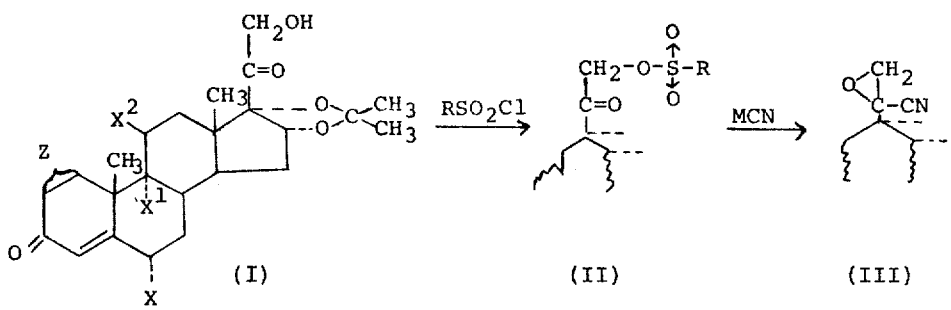

reaction is carried out in a suitable container with constant agitation, preferably at 0° to 50°C and more preferably at about 20° to 25°C for a period of time sufficient for the reaction to be completed. Generally the period of time will be anywhere from 5 to about 25 hours and generally will be about 15 to 20 hours.

In some cases it may be valuable to form the 21-halide, i.e. the 21-bromide, from the 21-hydrocarbon sulfonate steroid and react the 21-bromide thus formed with the metal cyanide to form the 20-cyano-20,21-epoxy steroid. Generally the 21-bromide is formed by reacting the 21-hydrocarbon sulfonate steroid such as the 21-mesyloxy or tosyloxy steroid with lithium bromide in a suitable solvent under reflux conditions. A suitable solvent may be chosen from any substantially inert oxygenated hydrocarbon solvent, such as acetone or a functional equivalent thereof. The reaction may be completed within about 10 hours or less, e.g. 5 hours. The resulting 21-bromide is isolated and thereafter reacted with a suitable metal cyanide, as discussed above, in an effective polar, aprotic, organic solvent such as dimethylformamide, and others disclosed above for the reaction of the 21-mesyloxy with sodium cyanide. The reaction is carried out at temperatures of about 10° to about 40°C in an inert atmosphere. Suitably the temperature is about 25°C and the reaction is carried out in a nitrogen atmosphere. The reaction is sufficiently completed within about 3 hours or less. The resulting 20-cyano-20,21-epoxy steroid may be readily recovered by extracting with a suitable solvent, such as ethyl acetate, washing, and purifying using well known techniques.

Whatever method is employed, once the 20-cyano-20,21-epoxy steroid is isolated, it is generally a mixture of the two 20-isomers. The isomers appear to be readily separable using means known in the art for this purpose. Thus the isomers may be separated using suitable chromatographic techniques or crystallization techniques. For example, a silica gel column may be used and a suitable eluting solvent such as a 20:80 ethyl acetate/hexane mixture, a 50:50 acetone/benzene mixture, or a 20:80 acetone hexane mixture. The isomers may then be readily recrystallized from the eluting solvent.

Pharmaceutical Composition

The novel steroids of this invention may be formulated with suitable pharmaceutical vehicles known in the art to form particularly effective topical, anti-inflammatory compositions. Generally about 0.001%w to about 10%w of the steroids defined hereinbefore are combined with about 90%w to about 99.999%w suitable excipients which may include a pharmaceutically acceptable solvent and other pharmaceutically acceptable additives to form a pharmaceutical formulation which may be applied topically.

A pharmaceutically acceptable solvent is one which is substantially non-toxic and non-irritating under the conditions used and may be readily formulated into any of the classical drug formulations such as creams, ointments, lotions, gels, or the like. Particularly suitable solvents include water, glycerine, propylene carbonate, and glycol such as 1,2-propylene diol (i.e. propylene glycol), 1,3-propylene diol, or mixtures thereof; polyethylene glycol having a molecular weight of from 100 to 10,000; dipropylene glycol; etc.; and mixtures of the aforementioned with each other.

A cream, topical, anti-inflammatory mixture may be prepared as a semi-solid emulsion of oil in water or water in oil. A cream base formulation by definition is an emulsion which is a two phase system with one liquid (for example fats or oils) being dispersed as small globules in another substance (e.g. a glycol-water solvent phase which may be employed as the primary solvent for the novel steroids of this invention). Typically the cream formulation may contain other than the solvent with the steroids therein, fatty alcohols, surfactants, mineral oil or petrolatum and other typical pharmaceutical adjuvants such as anti-oxidants, antiseptics, or compatible adjuvants. A typical cream base formulation is given in the following table.

| Water/glycol mixture (15% or more glycol) | 50 – 99 |
|---|---|
| Fatty alcohol | 1 – 20 |
| Non-ionic Surfactant | 0 – 10 |
| Mineral oil | 0 – 10 |
| Typical pharmaceutical adjuvants | 0 – 5 |
| *Active Ingredients | 0.001 – 10 |

The fatty alcohol, non-ionic surfactant, and other adjuvants are discussed in copending application U.S. Ser. No. 551,811 filed Feb. 21, 1975 and as much of that application as is pertinent is incorporated herein by reference.

The novel steroids of this invention may also be formulated as ointments. A "classical" ointment is a semi-solid anhydrous composition which may contain mineral oil, white petrolatum, a suitable solvent such as a glycol and may include propylene carbonate and other pharmaceutically suitable additives such as surfactants, for example Span and Tween or wool fat (lanolin), along with stabilizers such as antioxidants and other adjuvants as mentioned before. Following is an example of a typical "classical" ointment base:

| White petrolatum | 40 – 94 |
|---|---|
| Mineral Oil | 5 – 20 |
| Glycol solvent | 1 – 15 |
| Surfactant | 0 – 10 |
| Stabilizer | 0 – 10 |
| Active Ingredients | 0.001 – 10.0 |

Other suitable ointment base formulations which contain propylene carbonate are described in a copending U.S. patent applications Ser. No. 85,246, filed Oct. 29, 1970 by Shastri et al entitled "Propylene Carbonate Ointment Vehicle" and Ser. No. 201,997, filed Nov. 24, 1971 by Chang et al entitled "Fatty Alcohol-Propylene Carbonate-Glycol Solvent Cream Vehicle". As much of those applications as is pertinent is incorporated herein by reference. Following is an ointment base formulation containing propylene carbonate found to be particularly effective for the compositions of this invention:

| Active Ingredients | 0.001 – 10.0 |
|---|---|
| Propylene Carbonate | 1 – 10 |
| Solvent | 1 – 10 |
| Surfactant | 1 – 10 |
| White Petrolatum | 70 – 97 |

Suitable solvents, surfactants, stabilizers, etc. are discussed in U.S. Serial No. 551,811 and such discussion is incorporated herein by reference.

A suitable "non-classical" anhydrous, water washable "ointment type" base is described in U.S. Pat. No. 3,592,930 to Katz and Neiman, and as much of that disclosure as is pertinent is incorporated herein by reference. A representative composition of this invention utilizing such a base is as follows:

| Glycol solvent | 40 – 85 |
|---|---|

-continued

| | |
|---|---|
| Fatty alcohol | 15 – 45 |
| Compatible plasticizer | 0 – 15 |
| Compatible coupling Agent | 0 – 15 |
| Penetrant | 0 – 20 |
| Active Ingredients | 0.001 – 10.0 |

The fatty alcohols which are suitable have been previously disclosed above in this specification and in U.S. Pat. No. 3,592,930. As much of those disclosures as is pertinent is incorporated herein by reference.

Method Of Treatment

Generally an inflamed condition in animals, particularly humans, is combated by contacting the inflamed area with an effective amount of the novel steroids of this invention. Preferably the steroids are first formulated to prepare a suitable pharmaceutical formulation, as discussed hereinbefore, which is then placed in contact with the inflammed area. An effective amount will depend upon the particular condition and the animal receiving the treatment but will vary between 0.001% to 5% by weight of the pharmaceutical composition and preferably will be between 0.01 and 1% by weight of the formulation. Using these levels in the formulation, a therapeutically effective and non-toxic amount, i.e. enough to effect an anti-inflammatory response, but not enough to harm the recipient, is applied to the inflamed area.

The compounds of this invention not only have anti-inflammatory activity but also appear to exhibit a low level of systemic activity. This allows for the application of an effective amount of the anti-inflammatory compound without an adverse effect on the rest of the animal system.

The following Examples are given to illustrate the present invention but are not intended to limit the scope of the claims since other variations may be apparent to one of ordinary skill.

EXAMPLE I

Preparation of the 21-mesylate steroids

A. 2.0 Grams (g) of 9α,11β-dichloro-6α-fluoro-21-hydroxy-16α,17α-isopropylidenedioxy-pregna-1,4-dien-3,20-dione were added to a mixture of 2 mls triethyl amine and 50 mls of methylene chloride in a 100 ml flask. The mixture was cooled to −10°C and 1.5 g mesyl chloride is added to the mixture with constant stirring. The temperature was maintained at −10°C for 30 minutes until thin layer chromatography with 100% diethyl ether showed the reaction was complete.

The reaction mixture was poured into 100 ml of water then extracted with 250 ml ethyl acetate. The organic phase was washed with 200 ml of saturated sodium chloride then dried over 30 grams of dry sodium sulfate for 20 minutes. The solvent was removed by a rotary evaporator for 30 minutes at 30 mm Hg and 40°C.

The residue thus obtained was recrystallized from a mixture of 10 ml of ethyl acetate and 2 ml hexane to yield 1.774 g of 9α,11β-dichloro-6α-fluoro-16α,17α-isopropylidenedioxy-21-mesyloxy-pregna-1,4-dien-3,20-dione, m.p. 228°–230°C (decomposed).

B. By following the procedure set forth in part A of this example the following 21-mesylate steroids are prepared:

6α,9α-difluoro-11β-hydroxy-16α,17α-isopropylidenedioxy-21-mexyloxy-pregna-1,4-dien-3,20-dione;
6α,9α-difluoro-11β-hydroxy-16α,17α-isopropylidenedioxy-21-mesyloxy-pregn-4-en-3,20-dione;
6α-fluoro-11β-hydroxy-16α,17α-isopropylidenedioxy-21-mesyloxy-pregna-1,4-dien-3,20-dione;
6α-fluoro-11β-hydroxy-16α,17α-isopropylidenedioxy-21-mesyloxy-pregna-4-en-3,20-dione;
9α,11β-dichloro-6α-fluoro-16α,17α-isopropylidenedioxy-21-mesyloxy-pregn-4-en-3,20-dione;
6α-chloro-11β-hydroxy-16α,17α-isopropylidenedioxy-21-mesyloxy-pregna-1,4-dien-3,20-dione;
6α-chloro-20-cyano-20,21-epoxy-11β-hydroxy-16α,17α-isopropylidenedioxy-21-mesyloxy-pregn-4-en-3,2-dione;
9α-chloro-11β-hydroxy-16α,17α-isopropylidenedioxy-21-mesyloxy-pregna-1,4-dien-3,20-dione;
9α-chloro-11β-hydroxy-16α,17α-isopropylidenedioxy-21-mesyloxy-pregn-4-en-3,20-dione;
6α,9α-dichloro-11β-hydroxy-16α,17α-isopropylidenedioxy-21-mesyloxy-pregna-1,4-dien-3,20-dione;
6α,9α-dichloro-20-cyano-20,21-epoxy-11β-hydroxy-16α,17α-isopropylidenedioxy-21-mesyloxy-pregn-4-en-3,20-dione;
9α-fluoro-11β-hydroxy-16α,17α-isopropylidenedioxy-21-mesyloxy-pregna-1,4-dien-3,20-dione;
9α-fluoro-11β-hydroxy-16α,17α-isopropylidenedioxy-21-mesyloxy-pregn-4-en-3,20-dione;
6α,9α-fluoro-11β-hydroxy-16α,17α-isopropylidenedioxy-21-mesyloxy-pregna-1,4-dien-3,20-dione;
6α,9α-fluoro-11β-hydroxy-16α,17α-isopropylidenedioxy-21-mesyloxy-pregn-4-en-3,20-dione;
11β-hydroxy-16α,17α-isopropylidenedioxy-21-mesyloxy-pregna-1,4-dien-3,20-dione;
11β-hydroxy-16α,17α-isopropylidenedioxy-21-mesyloxy-pregn-4-en-3-dione;

EXAMPLE II

Preparation of the 21-tosylate steroids

A. 2.0 Grams of 11β,21-dihydroxy-16α,17α-isopropylidenedioxy-pregn-4-en-3,20-dione were added to 10 ml pyridine in a suitable flask. 1.0 G of toluene sulfonyl chloride (tosyl chloride) was added and the mixture was stirred at room temperature under nitrogen for about 16 hours. The reaction mixture was poured into ice cold 5% hydrochloric acid and extracted with 150 ml ethyl acetate. The organic phase was washed with saturated sodium chloride, dried over sodium sulfate, and the solvent removed using a rotary evaporator. The residue was then recrystallized from an acetone/hexane mixture to give 1.778 g of 11β-hydroxy-16α,17α-isopropylidenedioxy-21-toxyloxy-pregn-4-en-3,20-dione which had a m.p. of 203°–206.5°C (decomposed).

B. By following the procedure set forth in part A of this example, the following 21-tosylate steroids are prepared:
11β-hydroxy-16α,17α-isopropylidenedioxy-21-tosyloxy-pregna-1,4-dien-3,20-dione;
6α,9α-difluoro-11β-hydroxy-16α,17α-isopropylidenedioxy-21-tosyloxy-pregna-1,4-dien-3,20-dione;
6α,9α-difluoro-11β-hydroxy-16α,17α-isopropylidenedioxy-21-tosyloxy-pregn-4-en-3,20-dione;
6α-fluoro-11β-hydroxy-16α,17α-isopropylidenedioxy-21-tosyloxy-pregna-1,4-dien-3,20-dione;
6α-fluoro-11β-hydroxy-16α,17α-isopropylidenedioxy-21-tosyloxy-pregn-4-en-3,20-dione;

9α-fluoro-11β-hydroxy-16α,17α-isopropylidene-
dioxy-21-tosyloxy-pregna-1,4-dien-3,20-dione;

9α-fluoro-11β-hydroxy-16α,17α-isopropylidene-
dioxy-21-tosyloxy-pregn-4-en-3,20-dione;

9α,11β-dichloro-6α-fluoro-16α,17α-isopropylidene-
dioxy-21-tosyloxy-pregn-4-en-3,20-dione;

6α-chloro-11β-hydroxy-16α,17α-isopropylidene-
dioxy-21-tosyloxy-pregna-1,4-dien-3,20-dione;

6α-chloro-20-cyano-20,21-epoxy-11β-hydroxy-
16α,17α-isopropylidenedioxy-21-tosyloxy-pregn-4-en-
3,20-dione;

9α-chloro-11β-hydroxy-16α,17α-isopropylidene-
dioxy-21-tosyloxy-pregna-1,4-dien-3,20-dione;

9α-chloro-11β-hydroxy-16α,17α-isopropylidene-
dioxy-21-tosyloxy-pregn-4-en-3,20-dione;

6α,9α-dichloro-11β-hydroxy-16α,17α-isopropyli-
denedioxy-21-tosyloxy-pregna-1,4-dien-3,20-dione;

6α,9α-dichloro-20-cyano-20,21-epoxy-11β-hydroxy-
16α,17α-isopropylidenedioxy-21-tosyloxy-pregn-4-en-
3,20-dione;

6α,9α-fluoro-11β-hydroxy-16α,17α-isopropylidene-
dioxy-21-tosyloxy-pregna-1,4-dien-3,20-dione;

6α,9α-fluoro-11β-hydroxy-16α,17α-isopropylidene-
dioxy-21-tosyloxy-pregn-4-en-3,20-dione;

EXAMPLE III

Preparation of 20-cyano-20,21-epoxy-steroids

A. From 21-mesylate steroids 1.2 G of 9α,11β-dichloro-6α-fluoro-16α,17α-iso-propylidenedioxy-21-mesyloxy-pregna-1,4-diene-3,20-dione, prepared as in Example I, A were dissolved in 15 ml dimethylformamide (DMF). 1 G sodium cyanide was added and the mixture was stirred under nitrogen for about 16½ hours at room temperature. The reaction mixture was poured into water and extracted with 150 ml ethyl acetate, the organic phase was washed with saturated sodium chloride, dried over sodium sulfate and the solvent was removed on the rotary evaporator. The residue was then chromatographed on 80 G silica gel using 500 ml of acetone/benzene (50:50) as eluant. Recrystallization from acetone/benzene gave 85 mg an isomer of the compound 9α,11β-dichloro-20-cyano-20,21-epoxy-6α-fluoro-16α,17α-isopropyli-denedioxy-pregna-1,4-dien-3,20-dione (designated isomer A) having a m.p. 256°-58°C.

Recrystallization of the remaining material from acetone/hexane gave 129 mg of isomer B of the above 20-cyano-compound having a m.p. 237°-39°C.

By following the above procedure using the 21-mesyloxy steroids set forth in Example I,B, the corresponding 20-cyano-20,21-epoxy steroids may be prepared, for example isomer A of 20-cyano-20,21-epoxy-6α-fluoro-11β-hydroxy-16α,17α-isopropylidenedioxy-pregna-1,4-dien-3-one having a m.p. 290°-97°C;

isomer B of 20-cyano-20,21-epoxy-6α-fluoro-11β-hydroxy-16α,17α-isopropylidenedioxy-pregna-1,4-dien-3-one having a m.p. 284°-86°C;

isomer A of 20-cyano-20,21-epoxy-6α-fluoro-11β-hydroxy-16α,17α-isopropylidenedioxy-pregn-4-en-3-one having a m.p. 257°-63°C;

isomer B of 20-cyano-20,21-epoxy-6α-fluoro-11β-hydroxy-16α,17α-isopropylidenedioxy-pregn-4-en-3-one having a m.p. 242°C;

isomer A of 20-cyano-20,21-epoxy-11β-hydroxy-16α,17α-isopropylidenedioxy-pregna-1,4-dien-3-one having a m.p. of 317°-19°C; and isomer B of 20-cyano-20,21-epoxy-11β hydroxy-16α,17α-isopropylidenedioxy-pregna-1,4-dien-3-one having a m.p. of 292°-95°C.

B. From 21-tosylate steroids

The procedure of part A of this example was employed using 1.778 g of the 11β-hydroxy-16α,17α-isopropylidenedioxy-21-tosyloxy-pregn-4-en-3,20-dione in 10 ml of DMF. The residue was chromatographed on 150 g silica gel with 250 ml of acetone/hexane (20/80). Recrystallization from ethyl acetate hexane (50/50) gave 150 mg of isomer A of 20-cyano-20,21-epoxy-11β-hydroxy-16α,17α-isopropylidenedioxy-pregn-4-en-3-one having a m.p. 262°-265°C while isomer B had a m.p. 278°-282°C.

EXAMPLE IV

Preparation of 21-bromo steroids

A. The reaction product from Example IA was dissolved in 50 ml of acetone. Four grams of anhydrous lithium bromide were added and the solution refluxed under nitrogen for about 5 hours.

The reaction mixture was poured into 200 ml of water and extracted twice with 200 ml of methylene chloride. The combined organic extracts were dried over anhydrous sodium sulfate and the solvents evaporated under reduced pressure to yield 21-bromo-9α,11β-dichloro-6α-fluoro-16α,17α-isopropylidene-dioxy-pregna-1,4-dien-3,20-dione.

B. By employing the procedure described in part A of this example, other 21-bromo steroids may be prepared which correspond to the mesylates or tosylates set forth in part B of Examples I and II.

EXAMPLE V

Preparation of 20-cyano-20,21-oxido steroids From 21-bromo steroid

A. The reaction product of Example IV A was dissolved in 50 ml dimethylformamide. One gram of sodium cyanide was added while stirring at room temperature under nitrogen for 2½ hours. The reaction mixture was poured into 200 ml water than extracted with 200 ml ethyl acetate, which in turn was washed with 100 ml water, 200 ml saturated sodium chloride, dried over 30 g sodium sulfate, and the solvent removed by a rotary evaporator for 30 minutes at 40°C and 40 mm Hg. The resulting product was chromatographed on 200 g of silica gel using 6 l of 20% ethyl acetate/hexane solution, the eluate being collected in successive 25 ml fractions. 187 Mg of a product referred to as isomer A was obtained by collecting fractions 80 through 120, evaporating the liquid on a rotary evaporator, dissolving the residue in 10 ml of a 1:1 mixture of ethyl acetate/cyclohexane, and recrystallizing by cooling the resulting solution to 20°C. The resulting crystals had a melting point of 256°-258°C (decomposed) and an optical rotation of 58° (d). By collecting fractions 230 through 275 of the eluate, evaporating the liquid on a rotary evaporator, dissolving the residue in 10 ml of a 1:1 mixture of ethyl acetate/cyclohexane, and recrystallizing by cooling the solution to 20°C, 90 mg of a product referred to as isomer B was obtained which had a melting point of 237°C (decomposes) and optical rotation of +39° (d). The decomposed designation indicated that the substance charred badly within a few seconds of melting.

By following the procedure set forth in Part A of this example, other 20-cyano-20,21-epoxy-steroids specifically named in the specification are prepared.

EXAMPLE VI $\Delta^1$-hydrogenation of 20-cyano-20,21-oxido-$\Delta^{1,4}$-steroids A. 0.286 Gm of 6α,9α-difluoro-11β-hydroxy-16α,17α-isopropylidenedioxy-21-mesyloxy-pregna-1,4-diene-3,20-dione (prepared as described in Example IB) was dissolved in 6 ml of DMF. 100 Mg of sodium cyanide was added and the mixture was stirred under nitrogen for about 20 hours at 20°C. The reaction mixture was poured into water and extracted with 150 ml ethyl acetate, the organic phase was washed with saturated sodium chloride, dried over sodium sulfate and the solvent removed on the rotary evaporator. The residue was then chromatographed on 70 gm. silica gel using 2 l of ethyl acetate/hexane (3:15); 2 l of 6:12 ethyl acetate/hexane; and 2 l of 8:10 ethyl acetate (EtOAc)/hexane. The eluate was collected in successive 25 ml fractions. Fractions 85 through 105 were collected, the solvent removed by rotary evaporator, the residue dissolved in 10 ml of a 1:1 mixture of ethyl acetate/cyclohexane, and the compound recrystallized by cooling to 20°C. The resulting crystals (23 mg) were designated isomer A of 20-cyano-20,21-epoxy-6α,9α-difluoro-11β-hydroxy-16α,17α-isopropylidenedioxy-pregna-1,4-dien-3-one having a m.p. of 314°–16°C (decomposes). Similarly, fractions 155 through 180 of the eluate were collected and treated. Recrystallization of the second isomer from EtOAc/cyclohexane (1:1) gave 72 mg of the corresponding isomer B having a melting point of 323°C (decomposes).

B. 0.20 G of 20-cyano-6α,9α-difluoro-11β-hydroxy-16α,17α-isopropylidenedioxy-20,21-oxido-pregna-1,4-dien-3-one having a melting point of 323°C (Isomer B), 15 ml ethanol, 6 ml benzene, and 0.025 g of tris-(triphenylphosphine) rhodium (I) chloride, were added to a 50 ml flask and allowed to react for 30 hours at room temperature with constant stirring and under hydrogen at 1 atmosphere pressure. The product was obtained by preparative thin layer chromatography on silica gel eluting with 20% acetone in benzene and showed a m.p. of 271°–273°C and $\alpha_D$ of +79.5°C.

C. Isomer A of the compound in B, m.p. 314°–16°C, above, was treated similarly to give a product having a m.p. of 284°–85°C and $\alpha_D$+72.7°C. Other $\Delta^{1,4}$-steroids as set forth in Example III and elsewhere in the specification are similarly converted to the corresponding $\Delta^4$-steroids.

EXAMPLE VII

Anti-inflammatory Activity as Indicated by Alcoholic Vasoconstrictor Assay

An indication of anti-inflammatory activity of representative compounds of this invention is obtained by conducting a human vasoconstrictor assay as described by S. W. McKenzie and R. B. Stoughton in an article entitled "Method for Comparing Percutaneous Absorption of Steroids" Arch. Dermat. 86, 608 (1962) and slightly modified as follows:

The forearms of 8 normal adult human subjects were prepared by gentle washing and drying. Ethanolic solution of 0.05 mg ingredient per 5 ml solution were prepared for the A isomer of 20-cyano-20,21-epoxy-6α,9α-difluoro-11β-hydroxy-16α,17α-isopropylidenedioxy-pregna-1,4-dien-3-one (m.p. 314°–16°C-decomposes), the B isomer of same (m.p. 323°C-d), and fluocinolone acetonide. Areas of the subjects' forearms to be used in the study were outlined by a prepunched Blenderm tape having 32 7×7 mm squares per arm and 10 λ of formulation were applied per 7×7 mm. square site. After the preparations dried, the forearms were covered with Saran and the margins sealed with tape. Eighteen hours after application, the tape is removed and the forearms are washed. Six hours later, the presence of vasoconstriction is noted by visual examination, a blanching or whitening of the skin indicating the compound is active. By this test it appears that the A isomer has about 0.8 times the activity of fluocinolone acetonide, while isomer B exhibits about 0.3 times the activity.

The following representative compounds also are active in the vasoconstriction assay:

the A isomer of 9α,11β-dichloro-20-cyano-20,21-epoxy-6α-fluoro-16α,17α-isopropylidenedioxy-pregna-1,4-dien-3-one (m.p. 256°–58°C-decomposes);

the B isomer of 9α,11β-dichloro-20-cyano-20,21-epoxy-6α-fluoro-16α,17α-isopropylidenedioxy-pregna-1,4-dien-3-one (m.p. 237°–39°C-decomposes);

the B isomer of 20-cyano-20,21-epoxy-6α,9α-difluoro-11β-hydroxy-16α,17α-isopropylidenedioxy-pregna-1,4-dien-3-one (m.p. 323°C-decomposes);

the A isomer of 20-cyano-20,21-epoxy-6α,9α-difluoro-11β-hydroxy-16α,17α-isopropylidenedioxy-pregna-1-en-3-one (m.p. 284°–85°C);

the B isomer of 20-cyano-20,21-epoxy-6α,9α-difluoro-11β-hydroxy-16α,17α-isopropylidenedioxy-pregn-1-en-3-one (m.p. 271°–73°C);

the A isomer of 20-cyano-20,21-epoxy-6α-fluoro-11β-hydroxy-16α,17α-isopropylenedioxy-pregna-1,4-dien-3-one (m.p. 290°–97°C);

the B isomer of 20-cyano-20,21-epoxy-6α-fluoro-11β-hydroxy-16α,17α-isopropylenedioxy-pregna-1,4-dien-3-one (m.p. 284°–86°C);

the A isomer of 20-cyano-20,21-epoxy-11β-hydroxy-16α,17α-isopropylidenedioxy-pregn-4-en-3-one (m.p. 262°–65°C); and the B isomer of 20-cyano-20,21-epoxy-11β-hydroxy-16α,17α-isopropylidenedioxy-pregn-4-en-3-one (m.p. 278°–82°C).

EXAMPLE VIII

Systemic and Anti-Inflammatory Activity

An indication of systemic activity as well as anti-inflammatory activity is obtained by subcutaneously administering a solution of about 0.02–0.5 mg of the test compound to intact male rats weighing about 80–90 gm daily for two days and about the same amount the third day followed 1 hour thereafter by injection into the right hand paw of 0.05 ml of a 1% solution of carageenan to inflame the paw. The rats were sacrificed at day 3 about 4 hours later at which time the thymus was removed and weighed as well as both hind paws. Thymolytic activity is determined by calculating the mean thymus ratio (mg thymus wt./gm. body weight) and comparing the ratio with a standard of cortisol. Anti-inflammatory activity is determined by obtaining the mean percent increase in weight of the inflamed paw over that of the contralateral non-inflamed hind paw. This percent increase is then compared to a standard such as cortisol.

Results show that the following compounds, which are representative of those encompassed within the scope of this invention, have anti-inflammatory activity while showing low systemic activity:

the A isomer of 9α,11β-dichloro-20-cyano-20,21-epoxy-6α-fluoro-16α,17α-isopropylidenedioxy-pregna-1,4-dien-3-one (m.p. 256°–58°C-decomposes);

the B isomer of 9α,11β-dichloro-20-cyano-20,21-epoxy-6α-fluoro-16α,17α-isopropylidenedioxy-pregna-1,4-dien-3-one (m.p. 237°–39°C-decomposes);

the A isomer of 20-cyano-20,21-epoxy-6α,9α-difluoro-11β-hydroxy-16α,17α-isopropylidenedioxy-pregna-1,4-dien-3-one (m.p. 314°–16°C-decomposes);

the B isomer of 20-cyano-20,21-epoxy-6α,9α-difluoro-11β-hydroxy-16α,17α-isopropylidenedioxy-pregna-1,4-dien-3-one (m.p. 323°C-decomposes);

the A isomer of 20-cyano-20,21-epoxy-6α,9α-difluoro-11β-hydroxy-16α,17α-isopropylidenedioxy-pregn-1-en-3-one (m.p. 284°–85°C);

the B isomer of 20-cyano-20,21-epoxy-6α,9α-difluoro-11β-hydroxy-16α,17α-isopropylidenedioxy-pregn-1-en-3-one (m.p. 271°–73°C);

the B isomer of 20-cyano-20,21-epoxy-6α-fluoro-11β-hydroxy-16α,17α-isopropylidenedioxy-pregna-1,4-dien-3-one (m.p. 284°–86°C);

For example isomer B of 20-cyano-20,21-epoxy-6α,9αdifluoro-11β-hydroxy-16α,17α-isopropylidenedioxy-pregna-1,4-dien-3-one exhibited about 20 times the thymolytic activity of cortisol, while fluocinolone acetonide is over 400 times the thymolytic activity of cortisol.

EXAMPLE IX

Topical Anti-inflammatory Activity Using the Croton Oil-inflamed Rat Ear Test

Intact male rats, 21 days old, were anesthetized with ether and the test material was inuncted into the left ear in the following way: 0.05 ml of the vehicle containing the compound in solution was applied to the inner surface of the ear and 0.05 ml of the vehicle was applied to the outer surface. The vehicle consisted of 20% pyridine, 5% distilled water, 74% diethyl ether and 1% croton oil. The rats of the control group received the vehicle only, when vehicle served as the inflammatory stimulus. Since the inflammatory agent and test material were given together, the test measures the ability of the test agent to prevent the development of the inflammation, not the ability of the agent to inhibit a pre-induced inflammation. Both ears were removed 6 hours after the agent was applied and a piece of uniform size was punched from each ear with a No. 4 cork borer. The pieces of ear were then weighed.

The increase in weight of the piece punched from the left (inflamed) ear over that of the right (non-inflamed control) ear served as the end-point of the test.

Isomer B of 20-cyano-20,21-epoxy-6α,9α-difluoro-11β-hydroxy-16α,17α-isopropylidenedioxy-pregna-1,4-dien-3-one was assayed twice for topical anti-inflammatory activity using dosages of 1 and 10 micrograms per rat. The results show that isomer B had approximately 1 to 1.5 times the topical anti-inflammatory potency of fluocinolone acetonide.

Other representative compounds of this invention which exhibit anti-inflammatory activity in this test are:

The A isomer of 20-cyano-20,21-epoxy-11β-hydroxy-16α,17α-isopropylidenedioxy-pregna-1,4-dien-3-one; and other compounds set forth in Examples VII and VIII.

I claim as my invention:

1. A compound selected from the group of compounds represented by the formula

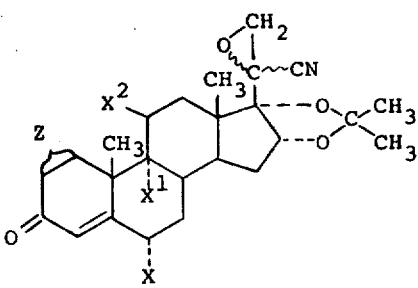 wherein

Z is double or single bond;
X is H, F or Cl;
X¹ is H, F or Cl; and
X² is OH or when X¹ is Cl, X² may be Cl.

2. The compound of claim 1 wherein X is H or F.

3. The compound of claim 2 wherein Z is a double bond, X is F, X¹ is Cl, and X² is Cl; 9α,11β-dichloro-20-cyano-20,21-epoxy-6α-fluoro-16α,17α-isopropylidenedioxy-pregna-1,4-dien-3-one and the 20-isomers thereof alone or in admixture.

4. The compound of claim 1 wherein Z is a double bond, both X and X¹ are F, and X² is OH; 20-cyano-20,21-epoxy-6α,9α-difluoro-11β-hydroxy-16α,17α-isopropylidenedioxy-pregna-1,4-dien-3-one and the 20-isomers thereof, alone or in admixture.

5. The compound of claim 1 wherein Z is a single bond, both X and X¹ are F, and X² is OH; 20-cyano-20,21-epoxy-6α,9α-difluoro-11β-hydroxy-16α,17α-isopropylidenedioxy-pregn-4-en-3-one and the 20-isomers thereof, alone or in admixture.

6. The compound of claim 1 wherein Z is a double bond, X is F, X¹ is H, and X² is OH; 20-cyano-20,21-epoxy-6α-fluoro-11β-hydroxy-16α,17α-isopropylidenedioxy-pregna-1,4-dien-3-one and the 20-isomers thereof, alone or in admixture.

7. The compound of claim 1 wherein Z is a single bond, X is F, X¹ is H and X² is OH; 20-cyano-20,21-epoxy-6α-fluoro-11β-hydroxy-16α,17α-isopropylidenedioxy-pregn-4-en-3-one and the 20-isomers thereof, alone or in admixture.

8. The compound of claim 1 wherein both X and X¹ are H.

9. The compound of claim 8 wherein Z is a single bond, and X² is OH; 20-cyano-20,21-epoxy-11β-hydroxy-16α,17α-isopropylidenedioxy-pregn-4-en-3-one and the 20-isomers thereof, alone or in admixture.

10. The compound of claim 8 wherein Z is a double bond, and X² is OH; 20-cyano-20,21-epoxy-11β-hydroxy-16α,17α-isopropylidenedioxy-pregna-1,4-dien-3-one and the 20-isomers thereof, alone or in admixture.

11. A topical, anti-inflammatory composition which comprises
   a. a compound selected from the group represented by the formula

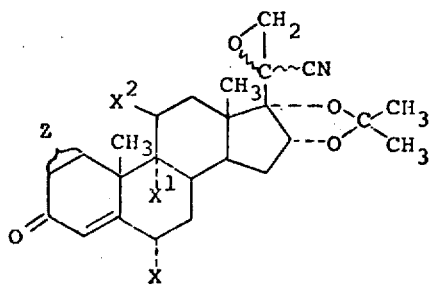

wherein

Z is double or single bond;
X is H, F or Cl;
$X^1$ is H, F, or Cl; and
$X^2$ is OH or when $X^1$ is Cl, $X^2$ may be Cl; and
   b. an effective amount of pharmaceutically suitable vehicle.

12. The composition of claim 11 which comprises
   a. about 0.001% by weight to 10.0% by weight of said compound and
   b. about 90.0% by weight to 99.999% by weight of said additives.

13. The composition of claim 11 wherein Z is a double or single bond; X is H or F; $X^1$ is H, Cl or F; and $X^2$ is OH; or when $X^1$ is Cl $X^2$ may also be Cl.

14. A process for treating inflammatory conditions in mammals, which process comprises topically administering an effective amount of at least one compound selected from the group represented by the formula

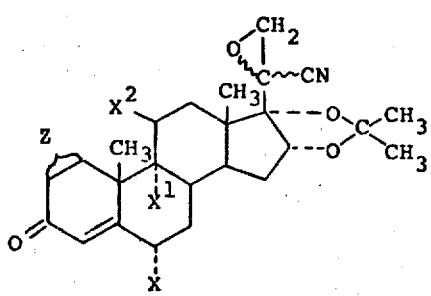

wherein

Z is double or single bond;
X is H, F or Cl;
$X^1$ is H, F or Cl; and
$X^2$ is OH or when $X^1$ is Cl, $X^2$ may be Cl;

15. The process of claim 14 wherein Z is a double or single bond; X is H or F; $X^1$ is H, Cl or F; and $X^2$ is OH or when $X^1$ is Cl $X^2$ may also be Cl.

16. A process for preparing 20-cyano-20,21-oxidosteroids which comprises reacting a compound chosen from those represented by the following formula

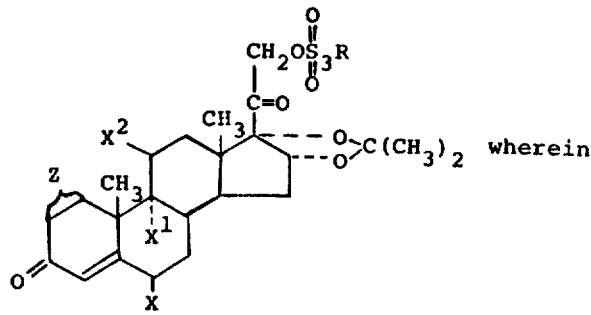
wherein

Z is a carbon-carbon double or single bond; X and $X^1$ are independently H, F or Cl;
$X^2$ is OH or when $X^1$ is Cl, $X^2$ may be Cl;
R is a hydrocarbon radical of 1–7 carbons;
with a suitable metal cyanide salt in a suitable polar, aprotic, organic solvent.

17. The process of claim 16 wherein R is $CH_3$ or

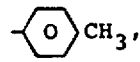

said cyanide salt is sodium cyanide, and said solvent is dimethylformamide.

18. A process for preparing a compound chosen from those represented by the formula

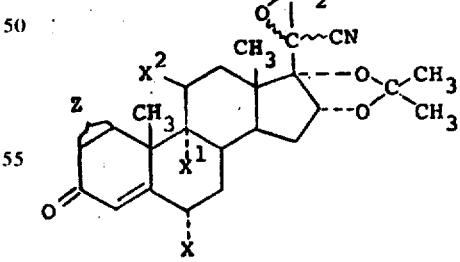

wherein
Z is a double or single bond;
X and $X^1$ are independently H, F or Cl; and
$X^2$ is OH and may be Cl when $X^1$ is Cl, which process comprises
   a. forming a compound of the formula

17

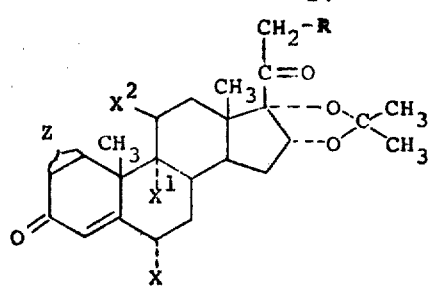

wherein

Z, X, X¹, and X² are defined as hereinbefore and R is

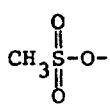

or

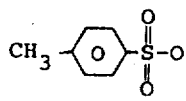

wherein and b. reacting the compound of part (a) with an alkali metal cyanide in a suitable polar, aprotic, organic solvent.

19. The process of claim 18 wherein said cyanide is sodium cyanide and said solvent is dimethylformamide.

20. The compound of claim 4 which is the 20-isomer alone which exhibits a melting point of 314° to 316°C when recrystallized from a mixture of equal parts ethyl acetate and cyclohexane.

21. The compound of claim 4 which is the 20-isomer alone which exhibits a melting point of 323°C when recrystallized from a mixture of equal parts ethyl acetate and cyclohexane.

* * * * *